United States Patent [19]

Beaty et al.

[11] Patent Number: 5,437,550
[45] Date of Patent: Aug. 1, 1995

[54] METHOD AND MEANS FOR AFFIXING A COMPONENT TO A DENTAL IMPLANT

[75] Inventors: Keith D. Beaty; Thomas S. Heylmun, both of West Palm Beach, Fla.

[73] Assignee: Implant Innovations, Inc., West Palm Beach, Fla.

[21] Appl. No.: 208,212

[22] Filed: Mar. 1, 1994

Related U.S. Application Data

[63] Continuation-in-part of Ser. No. 16,538, Feb. 11, 1993, Pat. No. 5,322,443.

[51] Int. Cl.⁶ .............................................. A61C 3/00
[52] U.S. Cl. ............................. 433/141; 433/173; 81/451
[58] Field of Search ............... 433/141, 173, 174; 81/451

[56] References Cited

U.S. PATENT DOCUMENTS 2,276,470  3/1942  Dodelin .......................... 81/451
4,072,070  2/1978  Finn ............................... 81/451
5,026,285  6/1991  Durr et al. .................... 433/141
5,062,800  11/1991 Niznick ......................... 433/173
5,064,375  11/1991 Jorneus ......................... 433/174
5,145,371  9/1992  Jorneus ......................... 433/174

*Primary Examiner*—Cary E. O'Connor
*Attorney, Agent, or Firm*—Alfred H. Rosen

[57] ABSTRACT

A tool for affixing a component to a dental implant fixture with a screw passing through the component and threaded into the implant fixture, in which the tool has two parts telescopically interfitting one within the other, the outer part being tubular for carrying the component at one end, and the inner part fitted at one end for carrying the screw positioned within the component, whereby the component and the screw within it can be carried together to the implant fixture where the outer part is used to hold the component in place while the inner part is used to drive the screw into the implant fixture.

29 Claims, 5 Drawing Sheets

METHOD AND MEANS FOR AFFIXING A COMPONENT TO A DENTAL IMPLANT

This application is a continuation in part of Ser. No. 08/016,538 filed on Feb. 11, 1993 now U.S. Pat. No. 5,322,443.

FIELD OF THE INVENTION

This invention relates to the art of restorative dentistry, and more particularly to that segment of the art which employs artificial roots to restore edentulous patients.

BACKGROUND OF THE INVENTION

At the present time, owing in part to its predictable success, the endosseous dental implant fixture in cylindrical form is the artificial root most frequently chosen for restoring dentition to edentulous patients when implant treatment is selected. These and other forms of artificial tooth roots are conveniently designed to receive and retain, sometimes removably, a variety of intermediate components including abutments which prosthodontists use to support artificial dentition on artificial roots. The intermediate components are necessarily small parts which must be manipulated into sometimes deep posterior locations in the patient's mouth and there assembled on an existing implant fixture or fixtures into rigid and reliable structures which can withstand the forces of mastication. More and more commonly the implant fixtures have internally threaded bores for receiving small screws which are used to attach the intermediate components to the implant fixtures, and to each other, and they have hexagonal or other non-circular means for anti-rotationally engaging such intermediate components. For biological reasons the implant fixtures and intermediate components are most often made of titanium and its dilute alloys, while the screws are made of the same metals or of gold, for example.

Typical diameters of implant fixtures are from about 3 mm to about 5 mm. Typical screw diameters are about 2 mm, or less. Typically, intermediate components have diameters in the same range as implant fixtures, and lengths short enough to be encompassed within an artificial tooth, or shorter. The problems of carrying such components to an implant fixture installed in a patient's jawbone and there affixing a component to the implant with a screw, and rotating the components to engage or mate with anti-rotational features on the implant fixture, without cross-threading the screw in the threaded bore of the implant fixture, are obvious.

Abutments and other intermediate components are made in a wide variety; some are small transmucosal components as small as one millimeter long, while some are several millimeters long intended to form the core of an artificial tooth; others may extend on an axis different from the longitudinal axis of the implant fixture, for adjusting the alignment of an artificial tooth relative to its neighbors; all must be affixed to the implant fixture. To do this the dental professional must hold the component in place on the implant fixture while inserting a screw through a small hole in the component and turning the screw in the threaded bore of the implant fixture until the screw is tight and the component is firmly affixed to it. This task becomes particularly onerous when the implant fixture is installed in a posterior region in the patient's mouth.

A dental clamp for gripping a cylindrical abutment is shown in U.S. Pat. No. 5,120,221 dated Jun. 9, 1992.

GENERAL NATURE OF THE INVENTION

The present invention employs two telescopically-interfitting parts, the inner one removably attached to the screw head and the other removably attached to a supragingival end of an intermediate component, for holding the screw and the component in relative positions suitable for installing them on the implant fixture and carrying them to the implant fixture in those positions, and there while holding the component in place on the implant fixture with the outer part using the inner part to turn the screw into the threaded bore of the implant fixture. Cross-threading of the screw is prevented by virtue of the fact that the component is firmly seated on the implant fixture with the aid of the outer part and the two telescopically interfitting parts align the screw accurately with relation to the threaded bore. The two interfitting parts can be designed to form an assembly including resilient means, such as a spring, to enable the inner part to press down on the outer part while turning the inner part, so that the entire installation procedure can be completed with two fingers (e.g: thumb and forefinger) while turning the inner part to install the screw. When the installation procedure is finished both parts can be detached from the screw and the component simply by pulling them away in the supragingival direction. It is not necessary to tighten the screw to its final torque limit with the carrying and affixing means of the present invention; that task can be performed with a separate torque-limited driver. The invention lends itself to packaging in a sealed container, which may be a sterile container if desired, so that a component and related screw may be delivered to a dental professional in a "ready for installation" condition. Thus, the present invention simplifies an onerous task while improving the accuracy with which that task is done, and saves the user valuable time while reducing the risk of infection.

BRIEF DESCRIPTION OF THE DRAWINGS

The appended drawings illustrate the background of the invention and exemplary embodiments of it. In these drawings.

DETAILED DESCRIPTION OF THE DRAWINGS

Figure 2:
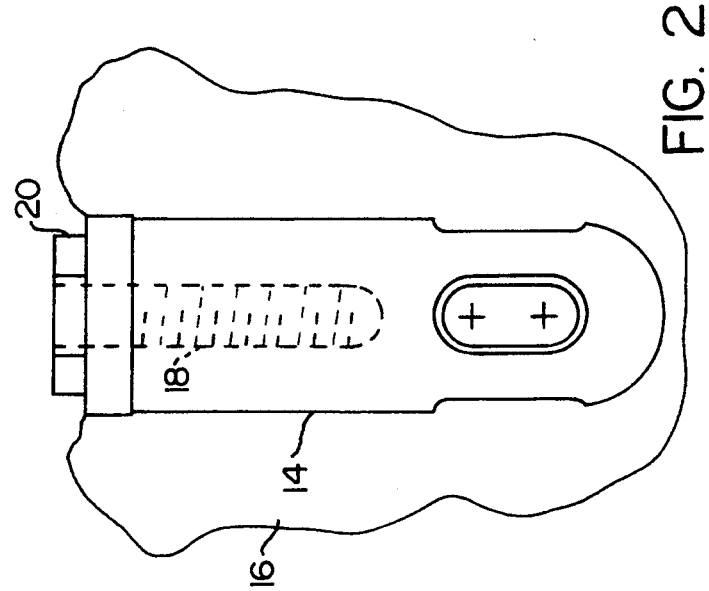
FIGS. 1 and 2 illustrate, respectively, a transmucosal component and related screw and a dental implant fixture on which they are to be installed.
Figure 1B:
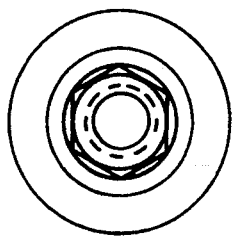
FIGS. 1A and 1B are end views of FIG. 1.
Figure 1:
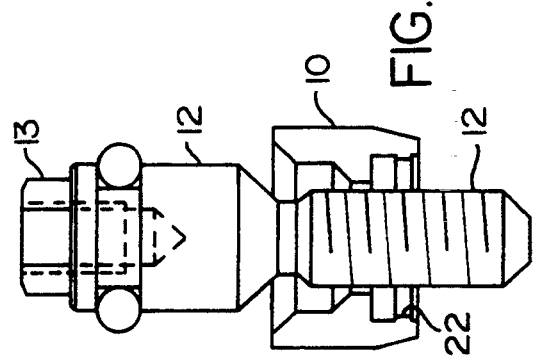
Figure 1A:
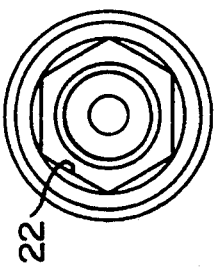
Figure 3:
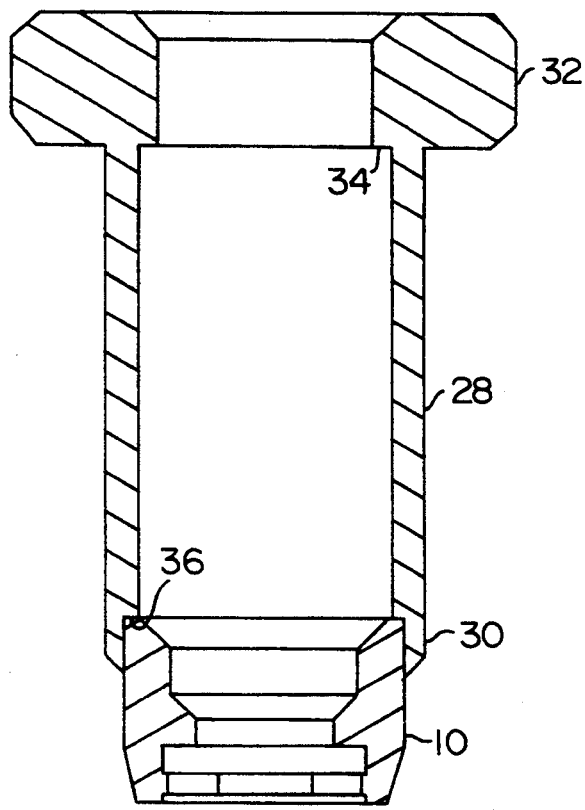
FIG. 3 illustrates a tubular part for holding the transmucosal component.

FIGS. 1 and 2 show a typical transmucosal component 10 and a typical screw 12 for use to install the transmucosal component on a dental implant fixture 14 which has been installed in jawbone 16. The screw and the transmucosal component are shown in relative positions suitable for installing them on the implant fixture, which has an internally-threaded bore 18 for receiving the screw. As is typical in the art, the implant fixture may have an anti-rotation boss 20 extending supragingivally from it, and the transmucosal component 10 may have a mating socket 22 for interfitting with the boss 20. In practice, the boss and the socket may be reversed. In either case, the transmucosal component must be fitted to the implant fixture with these anti-rotation devices engaged one in the other, prior to turning the screw 12 into the bore 18. FIG. 3 shows in longitudinal section a tubular holder part 28 for the transmucosal component 10. The internal diameter of this holder part is expanded at its lower end 30 to provide a recess with an internal shoulder 36 for receiving the supragingival end of the transmucosal component. The wall around the recess can be longitudinally slotted if desired to provide a circular array of resilient fingers (see FIG. 6) for releasibly holding the transmucosal component; alternatively the holder part 28 can be made of a resilient plastic material, in which case the wall around the recess can be continuous and the normal resilience of the plastic material will suffice to do the same thing. At its other end the holder has an expanded head 32 for gripping it and a second internal shoulder 34 for a purpose to be described.

Figure 4:
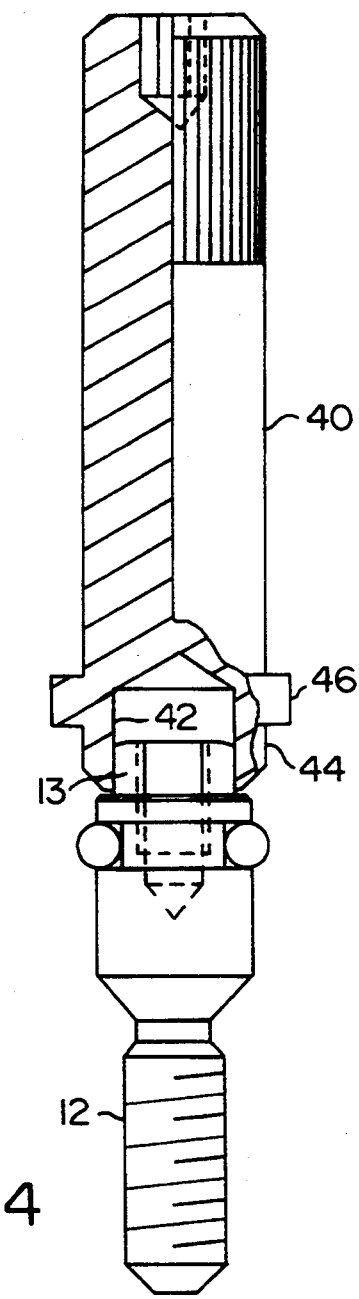
FIG. 4 illustrates a part for holding the screw.

The second holder part 40 shown in FIG. 4 is cylindrical in shape for telescopically fitting within the tubular holder part 28. This second part has a socket 42 in its lower end 44 for embracing the head 13 of the screw 12. This particular screw has a hexagonally-shaped head, and the socket 42 in the illustrated embodiment is matingly hexagonal. This is an optional feature adopted to accommodate a particular screw; the invention is not limited to it. For example, the male-female relation of the head 13 and the socket at 42 may be reversed. An annular boss 46 is also located near the lower end 44. When, as is illustrated in FIG. 5, the second holder part 40 is telescopically fitted within the tubular holder part 28 the boss 46 will stop against the second shoulder 34.

Figure 5:
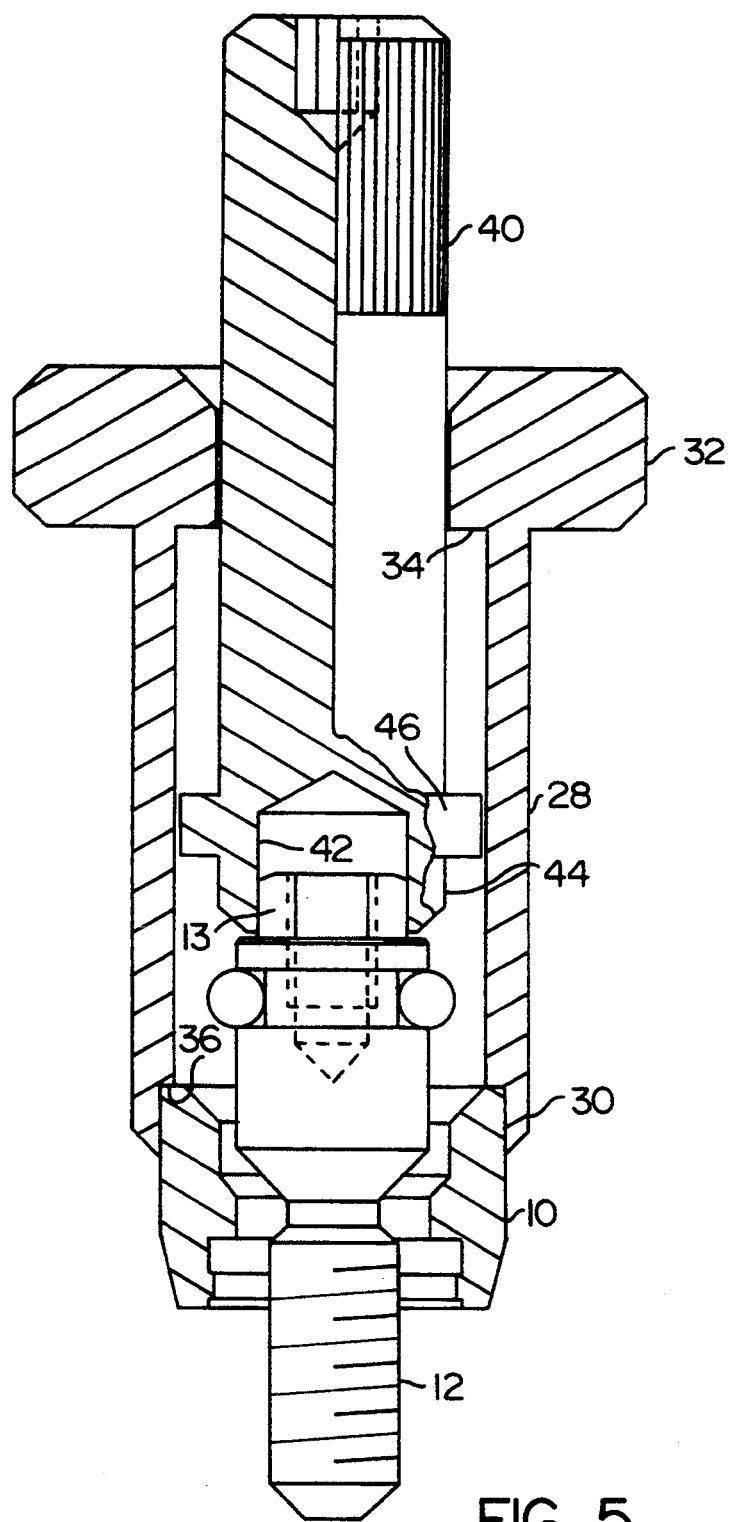
FIG. 5 shows the parts of FIGS. 3 and 4 telescopically interfitted and holding the transmucosal component and the screw in the relative positions they will occupy for installation on the implant fixture.

Referring now to FIG. 5, the two holder parts are shown with the second part 40 telescopically interfitted in the tubular part 28. To do this, the second part with the screw 12 engaged may be inserted through the lower end 30 of the tubular part 28, and thereafter the transmucosal component 10 may be attached to the tubular part. This arrangement provides an assembly of the holder-carrier 28, 40 and the dental components 10, 12 which can be brought as a unit to the dental implant fixture 14 with two fingers (e.g: thumb and forefinger) of one hand holding the assembly by the expanded head 32. At the implant fixture, the transmucosal component is then manipulated into place on the implant fixture and, while gently holding the transmucosal component against the implant fixture, the second holder part is turned to drive the screw 12 into the threaded bore 18. This assembly can be delivered as a unit to the end user, i.e: a prosthodontist, periodontist, oral surgeon or other qualified dental professional. It lends itself to encapsulation in a sterile package, if desired.

Figure 5A:
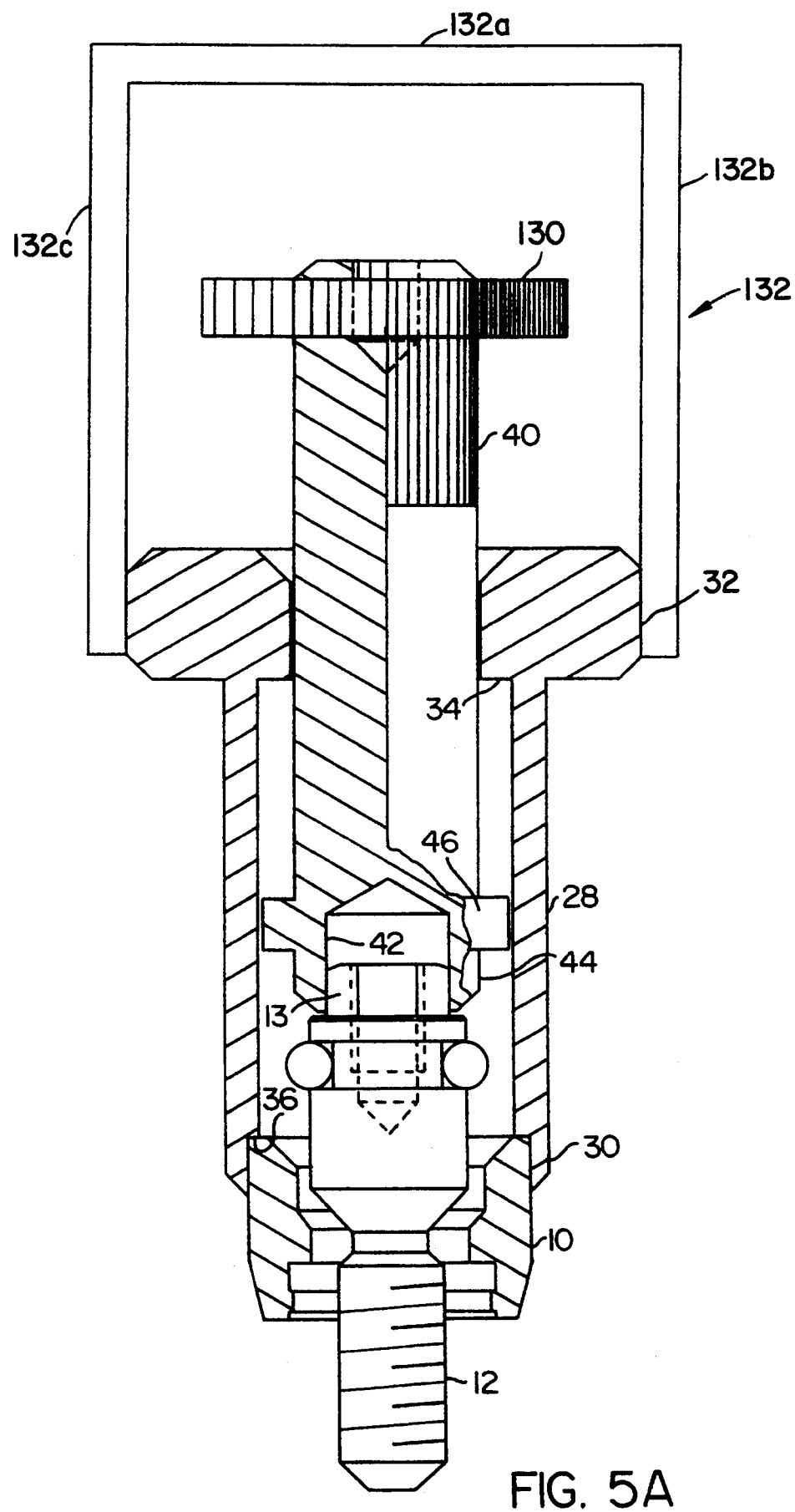
FIG. 5A is a modification of FIG. 5.

In FIG. 5A a manipulator 130 is fixed to the upper end of the second (driver) part 40, and holder means 132 having a bight portion 132a and two substantially parallel arms 132c and 132c is attached at the free ends of the arms to substantially diametrically opposite sides of the head 32 of the holder part 28. The bight portion 132a overlies the manipulator 130, and the manipulator fits between the arms 132c and 132c. In use, the holder means carries the assembled tool with the screw 12 and component 10 to a work site, where the bight portion 132a can be used to press the component to the implant with one finger while the manipulator can be turned with two other fingers of the same hand.

Figure 6:
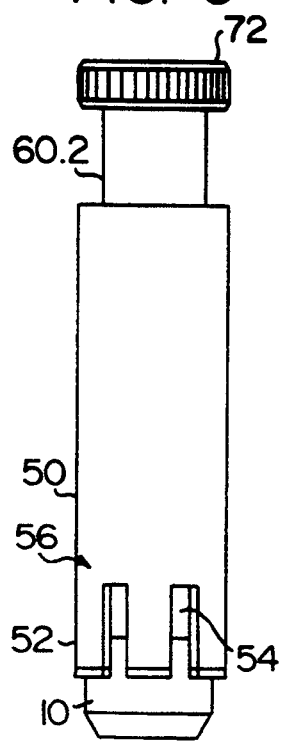
FIG. 6 is a side view of another embodiment of the invention.
Figure 7:
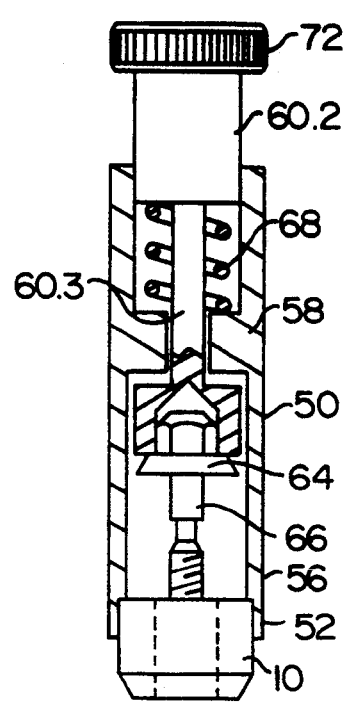
FIG. 7 is a longitudinal section through FIG. 6 showing a spring used to aid in a two-finger installation.
Figure 8:
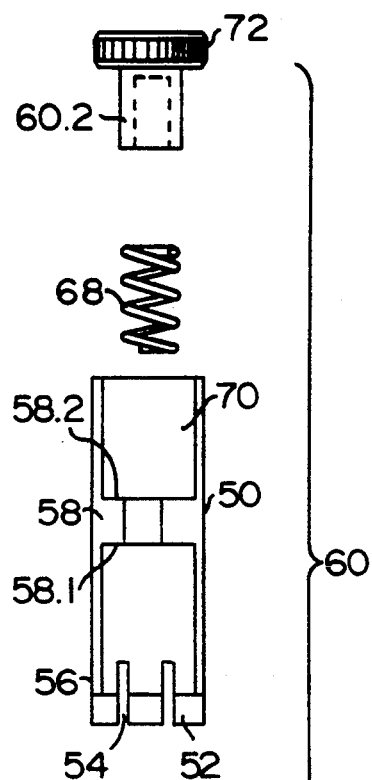
FIG. 8 is an exploded view of the parts of the embodiment shown in FIGS. 6 and 7.
Figure 8:
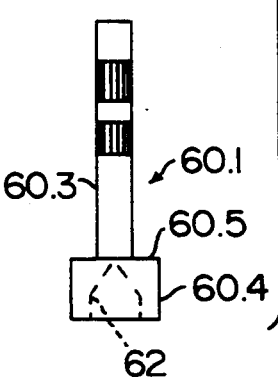

The embodiment of the invention that is illustrated in FIGS. 6, 7 and 8 is a unitary tool which includes a means to hold down the tubular part of the invention while turning the screw component with the second part of the invention. This embodiment is also designed to be compact so that it will minimally obscure the user's view of the task being performed, and will be easy and economical to package and ship. The outer tubular part 50 has spring-fingers 52 separated by longitudinal slots 54 at its lower end 56 for holding the abutment 10. The inner second part 60 is an assembly of two members, a head member 60.2 and a screw-holder member 60.1 having a stem 60.3. The tubular part 50 has a diametrically reduced section 58 between its ends providing a first shoulder 58.1 facing the lower end 56 and a second shoulder 58.2 facing in the opposite direction. The holder member 60.1 has a socket member 60.4 of larger diameter than its stem 60.3 affixed to the lower end of the stem, and forming a shoulder 60.5 where it joins the stem. The socket member has a non-round socket 62 for holding the matingly non-round head 64 of a screw 66 which is equivalent to the screw 12. To assemble this tool the stem 60.3 is passed through the lower end 56 of the tubular part 50 and through the reduced section 58 so that the shoulders 58.1 and 60.5 confront each other, a coil spring 68 is fitted over the stem 60.3 in the upper well 70 of the tubular part, and the head member 60.2 is press-fitted onto the free end of the stem. A turning knob 72 is provided on the free end of the head member.

In use, the screw 66 is fitted into the socket 62 and the component 10 is thereafter fitted into the spring fingers 52. This assembly is then carried to the installed implant fixture and the abutment is put in place on the implant fixture with the outer part 50. The knob 72 may then be grasped between the thumb and forefinger and pressed down toward the implant while the knob is turned to drive the screw into the implant fixture. The spring 68 provides resilient force to hold the component 10 on the implant while the screw is being turned.

The tool of FIGS. 6, 7 and 8 may be made of materials such as stainless steel which can be autoclaved. No lubricant is used in its construction. Alternatively this tool can be made of disposable materials and it can be delivered to the user in a sterile package including the component and screw to be installed on an implant fixture.

Figure 9:
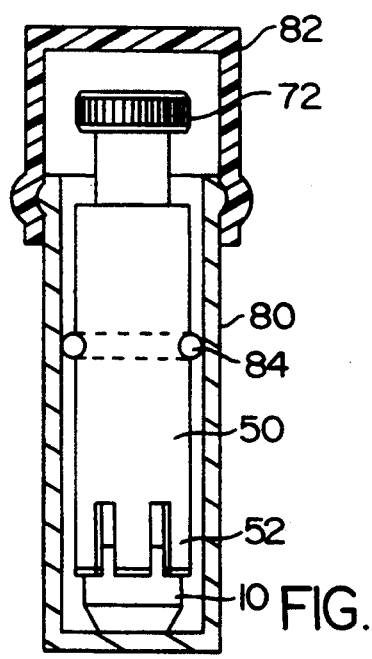
FIG. 9 is a longitudinal view partly in sections showing the embodiment of FIG. 6 in a sealed container.

FIG. 9 shows the tool of FIG. 6 enclosed in a capsule 80, which may be made of glass or plastic, for example, and is closed with a cap 82 which may be made of rubber or plastic, for example. The outer tubular part 50 is located with an O-ring 84 within the capsule. As is shown, the abutment 10 may be held against the bottom of the capsule, to prevent it from falling away from the spring fingers 52. In use, the cap 82 is removed and the tool is removed from the capsule with the turning knob 72 which is then used to carry the abutment 10 and screw 66 directly to the dental implant fixture 14.

We claim:

1. A tool for affixing a component to a support having a receiver member adapted to receive an attaching member for affixing said component, said tool forming an assembly comprising a first part for holding said component and a second part for holding said attaching member, and means to fix said parts in a substantially coaxial relation with said second part rotatable within first part, said second part having manipulator means at a first end of said second part, and holder means fixed to said first part and overlying said manipulator means for carrying said assembly and for holding said first part against said support while rotating said second part within said first part with said manipulator means.

2. A tool according to claim 1 in which said first part is hollow and said second part is fitted rotatably within said first part.

3. A tool according to claim 1 in which said first part is adapted at second end to detachably engage one end of said component and said second part is adapted at an end remote from said manipulating means to detachably engage one end of said attaching member.

4. A tool according to claim 1 in which the ends of said two parts at an end of said assembly remote from said manipulating means are adapted to detachably engage respectively one end of said component and one end of said attaching member.

5. A tool according to claim 1 including retainer means within said first part to keep said second part within said first part.

6. A tool according to claim 1 including compressible resilient means between said second part and said first part for coupling to said first part in the direction of said axis toward said first end thereof force applied to said second part in the direction of said axis toward said first end thereof.

7. A tool according to claim 6 in which said resilient means is a spring.

8. A tool according to claim 7 in which said spring is coiled around said second part.

9. A tool according to claim 8 in which said first part has a shoulder and said spring is fixed between said shoulder and said manipulating means.

10. A tool according to claim 8 in which said spring is coiled around said second part within said first part.

11. A tool according to claim 10 in which said first part has an internal shoulder and said spring is fixed between said shoulder and said manipulating means.

12. A tool according to claim 1 in which said holder means is a U-shaped member having two substantially parallel arms and a bight portion, the bight portion of which overlies said manipulator, the free ends of said arms being attached to said first part at points which are substantially diametrically opposite each other.

13. A tool according to claim 12 in which said manipulator fits between said arms.

14. Carrying and affixing tool means for use to affix a dental component to an artificial root installed in a patient's jawbone which root has an internally-threaded bore opening gingivally, said component having a through-bore for passing a threaded bolt, said bolt being engageable in said threaded bore for affixing said component to said root, said tool means forming an assembly comprising an elongated driver part adapted at a first end for engagement with a head end of said bolt and a hollow holder part adapted at a first end for engagement with said component at a supragingival end thereof, said driver part being rotatable within said holder part for holding said bolt within said throughbore when said component and said bolt are engaged with said tool means, so as to enable driving said bolt into said threaded bore with said driver part while holding said component to said root with said holder part, said driver part having manipulator means remote from said first end and accessible at a second end of said holder part, and holder means fixed to said holder part and overlying said manipulator means for carrying said assembly and for holding said holder part against said root while rotating said driver part within said holder part with said manipulator means.

15. Tool means according to claim 14 in which said driver part is elongated on an axis.

16. Tool means according to claim 15 including retainer means to keep said driver part within said holder part.

17. Tool means according to claim 16 in which said retainer means is a section of reduced cross-section within said holder part.

18. Tool means according to claim 15 having said manipulator means at the second end of said driver part.

19. Tool means according to claim 18 including compressible resilient means between said driver part and said holder part for coupling to said holder part in the direction of said axis toward said one end thereof force applied to said driver part in the direction of said axis towards said one end thereof.

20. Tool means according to claim 19 in which said resilient means is a spring.

21. Tool means according to claim 20 in which said spring is coiled around said driver part within said holder part.

22. Tool means according to claim 21 in which holder part has an internal shoulder and said spring is fixed between said shoulder and said manipulator means.

23. Tool means according to claim 14 in which said holder means is a U-shaped member having two substantially parallel arms and a bight portion, the bight portion of which overlies said manipulator, the free ends of said arms being attached to said first part at points which are substantially diametrically opposite each other.

24. Tool means according to claim 23 in which said manipulator fits between said arms.

25. An assembly of a dental component adapted to be affixed to a substructure fixed in a patient's jawbone, an attaching member cooperable with said substructure for affixing said component thereto, and tool means comprising a first part for holding said component and a second part for holding said attaching member, said component being removably engaged endwise with said first part and said attaching member being removably engaged endwise with said second part, said tool means including means to fix said parts in a spatial relation with one part rotatable relative to the other such that if said first part is manipulated to bring said component to said substructure said second part will be disposed to manipulate said attaching member to affix with said component to said substructure, said second part having manipulator means accessible at an end of said first part remote from said component, and holder means fixed to said first part and overlying said manipulator means for carrying said assembly and for holding said first part against said substructure while rotating said second part relative to said first part with said manipulator means.

26. An assembly according to claim 25 and a removable enclosure surrounding said assembly.

27. An assembly and an enclosure according to claim 25 in which said enclosure is a sterile package.

28. An assembly according to claim 25 in which said holder means is a U-shaped member having two substantially parallel arms and a bight potion, the bight potion of which overlies said manipulator, the free ends of said arms being attached to said first part at points which are substantially diametrically opposite each other.

29. An assembly according to claim 28 in which said manipulator fits between said arms.

* * * * *